(12) United States Patent
Mazzarolo et al.

(10) Patent No.: US 8,291,521 B2
(45) Date of Patent: Oct. 23, 2012

(54) ADJUSTABLE NECK PROTECTIVE COLLAR IN PARTICULAR FOR MOTORCYCLE RIDERS

(75) Inventors: Giovanni Mazzarolo, Coste di Maser (IT); Colin Ballantyne, Caselle d'Asolo (IT)

(73) Assignee: Alpinestars Research Srl, Coste di Maser (Treviso) (IT)

( * ) Notice: Subject to any disclaimer, the term of this patent is extended or adjusted under 35 U.S.C. 154(b) by 163 days.

(21) Appl. No.: 12/743,483

(22) PCT Filed: Mar. 6, 2009

(86) PCT No.: PCT/IB2009/050936
§ 371 (c)(1),
(2), (4) Date: May 18, 2010

(87) PCT Pub. No.: WO2009/109943
PCT Pub. Date: Sep. 11, 2009

(65) Prior Publication Data
US 2010/0235973 A1    Sep. 23, 2010

(30) Foreign Application Priority Data
Mar. 6, 2008 (IT) .................................. TV08A0039

(51) Int. Cl.
*A42B 3/12* (2006.01)
*A42B 3/14* (2006.01)
*A42B 3/00* (2006.01)

(52) U.S. Cl. ............. 2/425; 2/410; 2/415; 2/421; 2/468; 2/44; 2/45

(58) Field of Classification Search ...... 2/455, 459–463, 2/410, 411–415, 421, 468, 44, 45, 129, 265, 2/266, 267, 268
See application file for complete search history.

(56) References Cited

U.S. PATENT DOCUMENTS

| | | | |
|---|---|---|---|
| 2,820,455 A | | 12/1953 | Hall |
| 3,076,206 A | * | 2/1963 | Shaw et al. .................... 441/104 |
| 3,202,307 A | * | 8/1965 | Rainer et al. ................... 215/328 |
| 3,477,425 A | | 11/1969 | Grassi |
| 3,495,272 A | | 2/1970 | Tempelhof |
| 3,765,412 A | | 10/1973 | Ommaya et al. |
| 3,849,801 A | * | 11/1974 | Holt et al. ......................... 2/413 |

(Continued)

FOREIGN PATENT DOCUMENTS
DE    27 17 712 A1    10/1978
(Continued)

OTHER PUBLICATIONS
English-language Abstract FR2700746 (Schegerin).
(Continued)

*Primary Examiner* — Bobby Muromoto, Jr.
(74) *Attorney, Agent, or Firm* — Fredrikson & Byron, PA (57) ABSTRACT

A collar for protecting the neck of a user, useful in particular for motorcycle riders, is envisaged, said collar comprising two half-collars which are pivotably hinged together at one end so as to be rotatable in a substantially horizontal plane and which can be connected together by means of a fastening and release lever, a plate which at the rear extends downwards from the bottom edge of the collar so as to be centred with respect to the spinal column of the user, and a protective shield which extends downwards at the front. The collar is provided with removable padding means where the collar rests on the user's shoulders.

9 Claims, 6 Drawing Sheets

U.S. PATENT DOCUMENTS

| | | | | |
|---|---|---|---|---|
| 3,855,631 | A | 12/1974 | Ettinger | |
| 3,858,241 | A | 1/1975 | Durand | |
| 3,878,561 | A | 4/1975 | Winiecki | |
| 4,274,161 | A | 6/1981 | Littler | |
| 4,319,362 | A | 3/1982 | Ettinger | |
| 4,422,454 | A | 12/1983 | English | |
| 4,441,211 | A * | 4/1984 | Donzis | 2/459 |
| 4,449,251 | A | 5/1984 | Gauthier | |
| 4,501,023 | A * | 2/1985 | Bilberry | 2/462 |
| 4,502,471 | A * | 3/1985 | Owens | 602/18 |
| 4,554,681 | A * | 11/1985 | Kirkland | 2/462 |
| 4,675,912 | A * | 6/1987 | Kirkland | 2/462 |
| 4,821,339 | A | 4/1989 | Fair | |
| 4,854,306 | A | 8/1989 | Pujals | |
| 4,989,265 | A * | 2/1991 | Nipper et al. | 2/462 |
| 4,996,720 | A | 3/1991 | Fair | |
| 5,003,968 | A | 4/1991 | Mars | |
| 5,039,035 | A | 8/1991 | Fitzpatrick | |
| 5,133,084 | A | 7/1992 | Martin | |
| 5,230,698 | A | 7/1993 | Garth | |
| 5,411,471 | A | 5/1995 | Terrazas | |
| 5,437,613 | A | 8/1995 | Reggio et al. | |
| 5,517,699 | A | 5/1996 | Abraham, II | |
| 5,531,669 | A | 7/1996 | Varnau | |
| 5,546,609 | A | 8/1996 | Rush, III | |
| 5,590,826 | A | 1/1997 | Endo | |
| 6,058,517 | A | 5/2000 | Hartunian | |
| 6,067,665 | A | 5/2000 | DePalma et al. | |
| 6,494,854 | B1 | 12/2002 | Visness et al. | |
| 6,729,643 | B1 | 5/2004 | Bassick | |
| 7,017,194 | B2 | 3/2006 | Schroth | |
| 7,041,073 | B1 | 5/2006 | Patron | |
| 7,329,230 | B2 * | 2/2008 | Mazzarolo | 602/19 |
| 7,371,221 | B1 | 5/2008 | Baker | |
| 2004/0167448 | A1 | 8/2004 | Hefez | |
| 2007/0010771 | A1 | 1/2007 | Leatt | |
| 2007/0106194 | A1 | 5/2007 | Pickering | |
| 2007/0281125 | A1 | 12/2007 | Moore | |
| 2010/0056968 | A1 | 3/2010 | Mazzarolo | |
| 2010/0121238 | A1 | 5/2010 | Mazzarolo | |
| 2010/0251468 | A1 | 10/2010 | Mazzarolo | |
| 2010/0263112 | A1 | 10/2010 | Mazzarolo | |
| 2011/0004980 | A1 | 1/2011 | Leatt et al. | |

FOREIGN PATENT DOCUMENTS

| | | |
|---|---|---|
| DE | 31 36 466 A1 | 4/1983 |
| DE | 295 21 373 U1 | 4/1997 |
| DE | 195 45 299 A1 | 6/1997 |
| DE | 200 06 084 U1 | 8/2001 |
| EP | 0023115 A | 1/1981 |
| EP | 0043990 A1 | 1/1982 |
| FR | 2534115 A | 4/1984 |
| FR | 2700746 | 7/1994 |
| FR | 2719747 | 11/1995 |
| GB | 2 126 485 A | 3/1984 |
| SL | 9600306 A | 4/1998 |
| WO | 9809545 A1 | 3/1998 |
| WO | 9938401 A1 | 8/1999 |
| WO | 0125088 | 4/2001 |
| WO | 02089620 A1 | 11/2002 |
| WO | 03077793 A2 | 9/2003 |
| WO | 03092561 | 11/2003 |
| WO | 2005051251 A | 6/2005 |
| WO | 2005107658 A | 11/2005 |

OTHER PUBLICATIONS

English-language Abstract FR2719747 (Streiff Motorsport).
English-language Abstract FR2534115 (Nolan SPA).
"PCT International Search Report dated May 12, 2009 for PCT/IB2009/050936, from which the instant application is based," 2 pgs.
"PCT Demand with attachments dated Dec. 28, 2009 for PCT/IB2009/050936, from which the instant application is based," 12 pgs.
"PCT International Search Report dated May 15, 2009 for PCT/IB2009/050934," 2 pgs.
"PCT Written Opinion dated May 15, 2009 for PCT/IB2009/050934," 5 pgs.
"PCT International Search Report dated May 13, 2009 for PCT/IB2009/050938," 3 pgs.
"PCT Demand with attachments dated Dec. 28, 2009 for PCT/IB2009/050938," 7 pgs.
"PCT Written Opinion dated May 13, 2009 for PCT/IB2009/050938," 4 pgs.
"PCT International Preliminary Report on Patentability dated May 26, 2010 for PCT/IB2009/050936, from which the instant application is based," 6 pgs.
"PCT International Preliminary Report on Patentability dated May 27, 2010 for PCT/IB2009/050938," 4 pgs.

* cited by examiner

ADJUSTABLE NECK PROTECTIVE COLLAR IN PARTICULAR FOR MOTORCYCLE RIDERS

RELATED APPLICATIONS

This application is a 35 U.S.C. 371 national stage filing from International Application No. PCT/IB2009/050936 filed Mar. 6, 2009 and claims priority to Italian Application No. TV2008A000039 filed Mar. 6, 2008, the teachings of which are incorporated herein by reference.

This invention relates to a neck protective collar, useful during sporting activities, especially when riding motorcycles.

Various protective collars intended for persons who practise sporting activities are known and are commercially available. The obvious objective is to protect a part of the human body, such as the neck, which is extremely delicate and prone to fractures and knocks. In the event of a fall, for example from a motorcycle travelling at speed, it is known that the neck often suffers damage, despite the fact that the rider is wearing a conventional protective helmet.

An example of a collar for motocross is described in the international patent application No. WO 2005/051251 in the name of Leatt.

This collar consists of two sections which are releasably connected together by means of a side hinge. The collar has surfaces which are directed upwards and limit the inclination of the head in all directions when the helmet is worn.

The collar rests on the user's shoulders by means of a padding permanently fixed to its bottom edge and has a plate extending at the rear downwards from its rear edge, with the function of transferring to the sides of the spinal column loads acting on the user's back, so that they are unable to act on the spine itself.

This type of collar, as well as other collars which are known from the prior art, however, have various problems and drawbacks.

In particular, empty spaces remain under the side parts of the collar and in particular the side hinge such that the collar is less stable on the user's body. This is especially noticeable on users which have a longer or shorter neck than average.

The object of the invention is to provide a collar which solves substantially the abovementioned problems and drawbacks and is easy to use, in addition to protecting the user in an effective manner.

In particular, object of the present invention is to provide a protective collar which can be easily adapted to the user's body and neck length.

This object is achieved with a collar for protecting the neck of a user, useful in particular for motorcycle riders, of the type comprising two half-collars which are pivotably hinged together at one end so as to be rotatable in a substantially horizontal plane and which can be connected together by means of a fastening and release lever, a plate which at the rear extends downwards from the bottom edge of the collar so as to be centred with respect to the spinal column of the user, and a protective shield which extends downwards at the front, characterized in that it comprises padding means being able to be removably connected to the bottom surface of said two half-collars in lateral zones intended to engage with the user's shoulders.

According to a further characteristic feature of the collar of the present invention, the aforementioned plate extending at the rear and resting on the user's back has a structure designed to break or collapse in a programmed manner in a direction parallel to the spinal column of the user following an impact.

The advantages of the invention will be explained more fully by the following description, intended purely by way of a non-limiting example, of a preferred embodiment of a collar, shown in the accompanying drawings in which.

Figure 1:
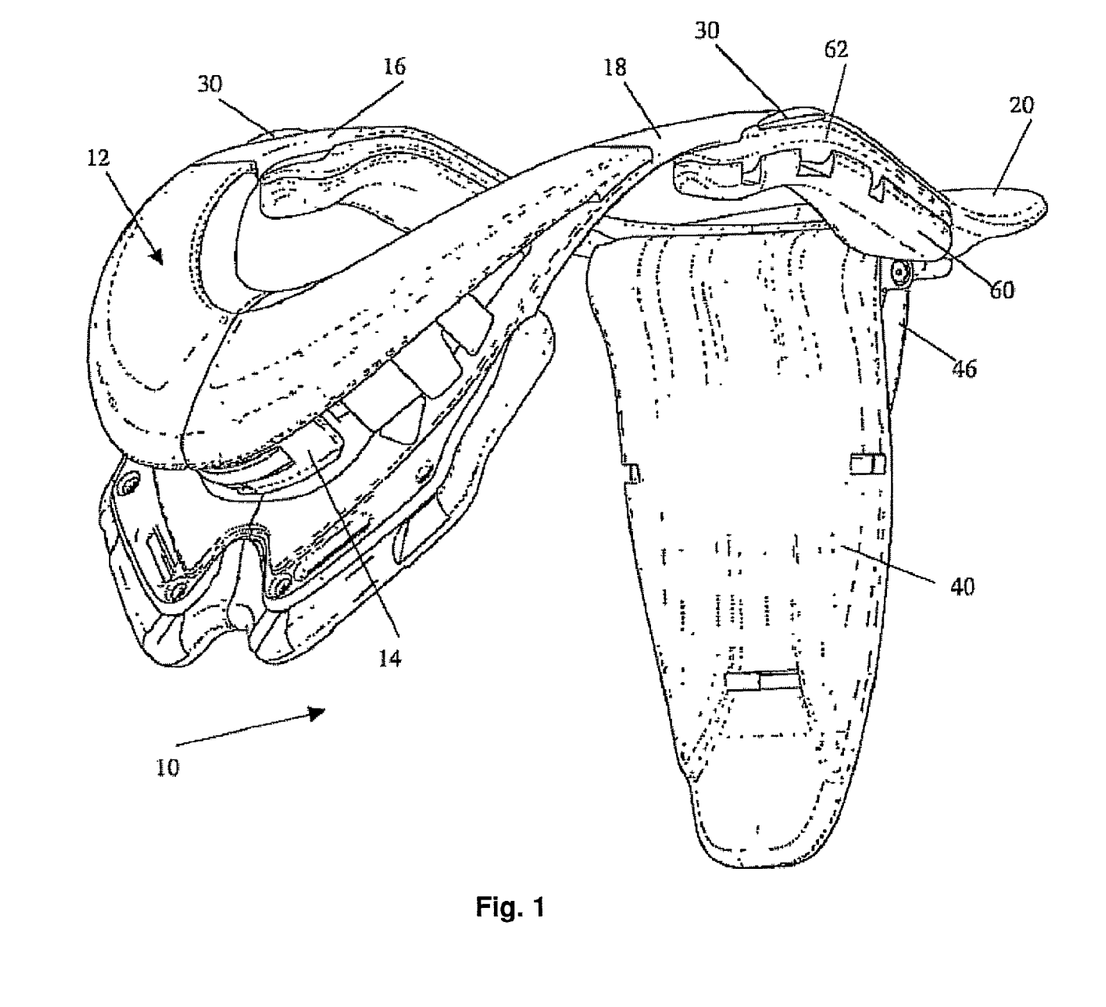
FIG. 1 shows a three-dimensional front view of the collar.
Figure 2:
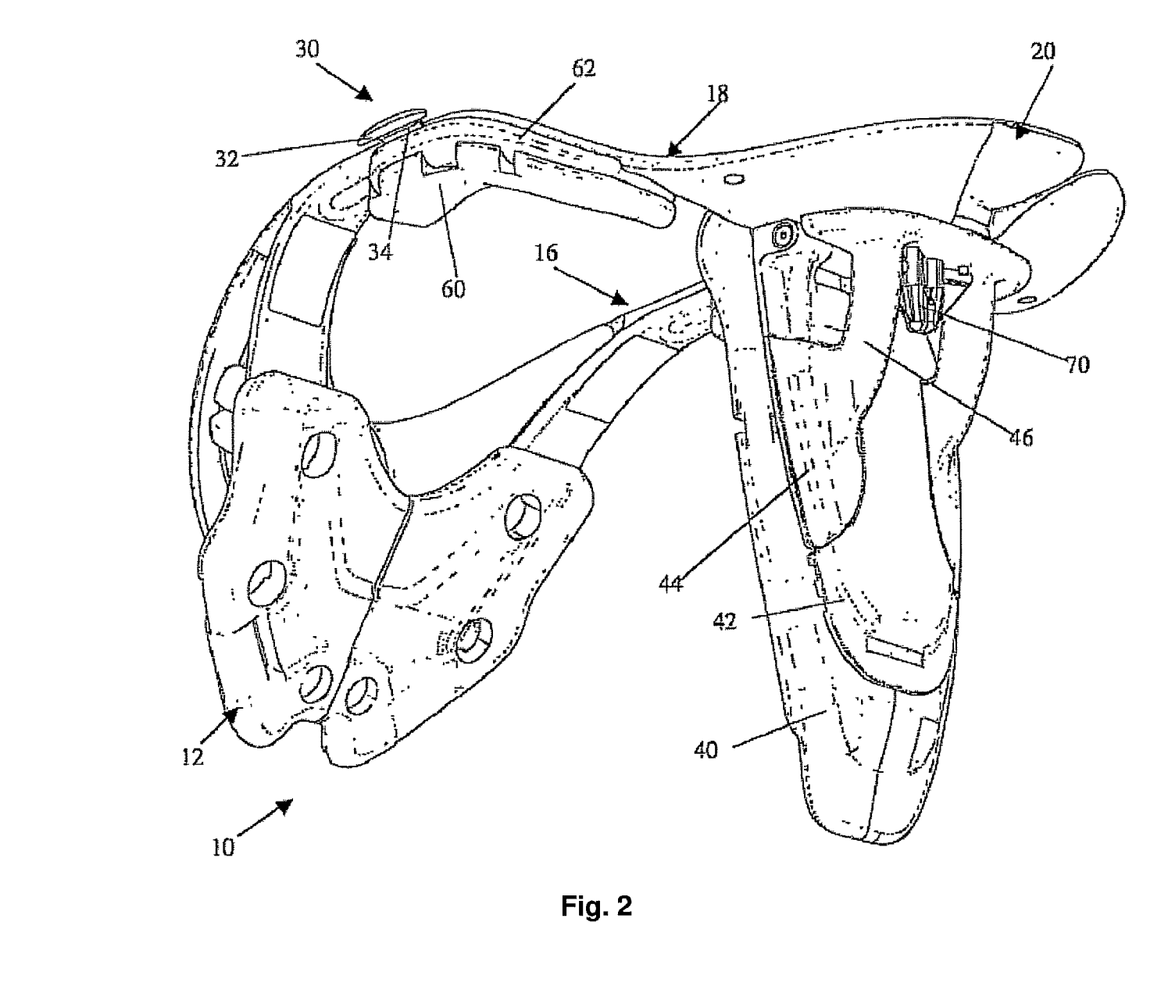
FIG. 2 shows a three-dimensional rear view of the collar according to FIG. 1.

With reference first of all to FIGS. 1 and 2, there is shown a collar 10 which has a symmetrical structure and consists of a front part 12, which rests on the chest, closed by a fastening lever 14, two side segments 16, 18 which are nearly flat, and a rear part 20.

The segments 16, 18 are hinged together by means of a rear pin 70 and may be opened wide apart so that the neck can be inserted inside the collar 10. The fastening lever 14 has the function of fastening together the segments 16, 18 in the closed position such that, during use, the collar 10 has an annular structure which surrounds the neck completely.

The segments 16, 18 have a cross-section in the form of a rounded rectangle and each of them has, mounted on the edge towards the outside of the collar 10, a tongue 30 which is formed by a central body 34 which terminates in a right-angled extension 32 widened in the form of a mushroom head.

Two pads 60, 62 are mounted underneath each of the segments 16, 18, being arranged on top of each other.

Figure 3:
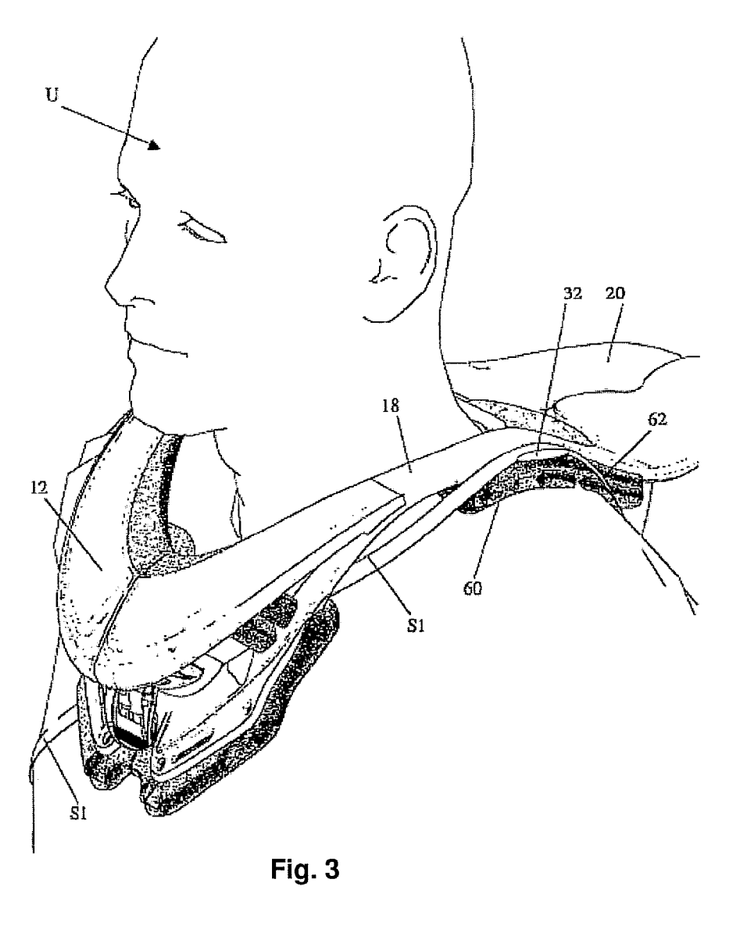
FIG. 3 shows the straps connected to the collar according to FIG. 1.
Figure 4:
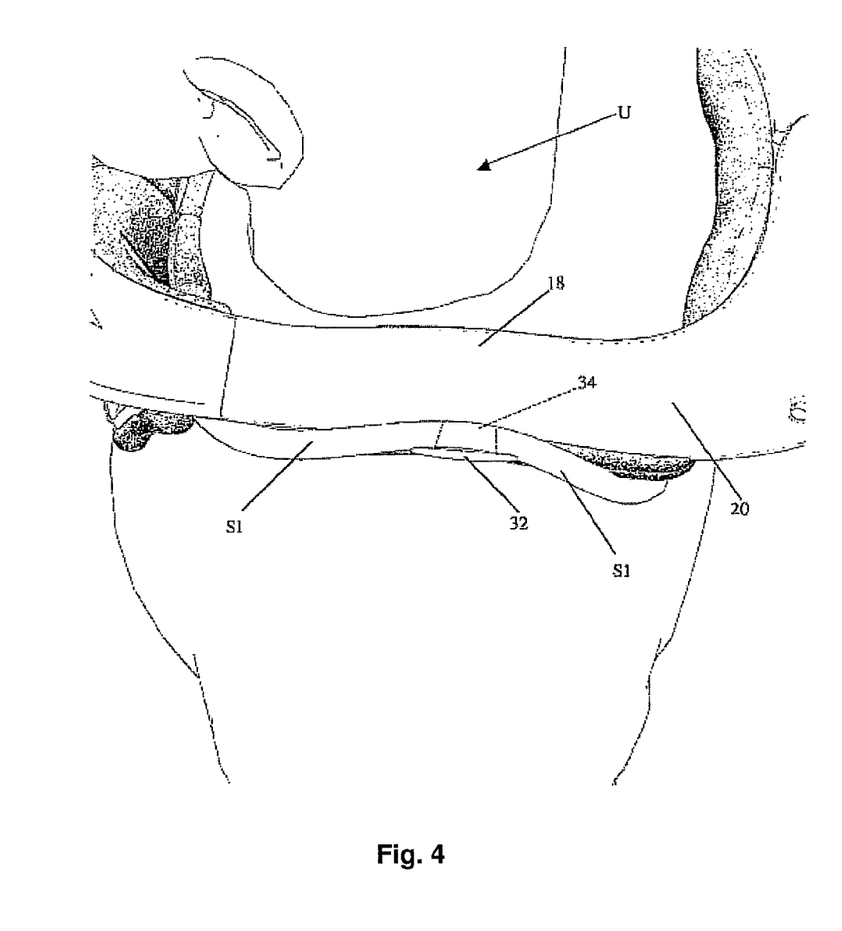
FIG. 4 shows a top plan view of FIG. 3.

A user U (FIG. 3) who wishes to fix the collar 10 may use two elastic straps S1, S2 which are arranged so as to cross over each other on the chest.

Considering now FIGS. 3-6, the pads 60, 62 (see FIG. 5) have a special structure. They are both curved so as to follow the profile of the associated segment 16, 18 and the shoulder.

Figure 5:
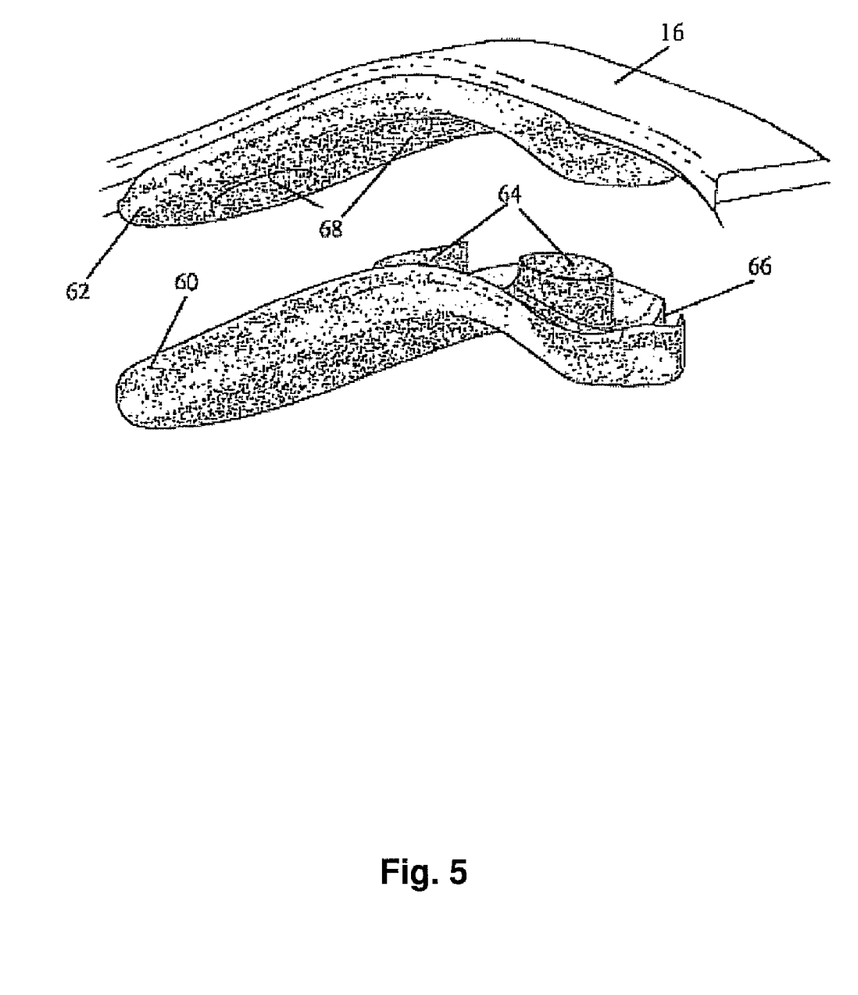
FIG. 5 shows cushioning pads removed from the collar.
Figure 6:
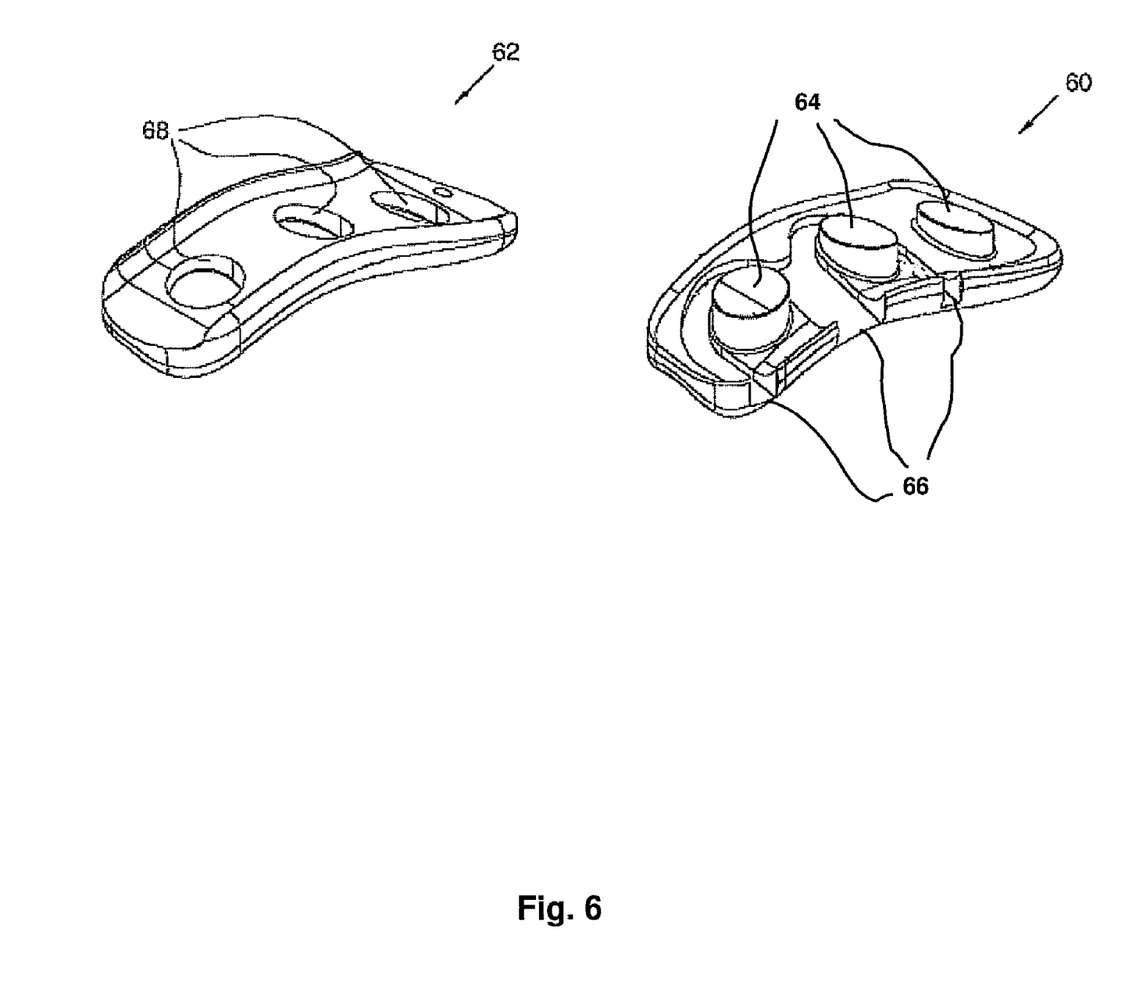
FIG. 6 shows the inner side of the pads according to FIG. 5.

The pad 62 is attached in a fixed manner to the bottom surface of the respective segment 16, 18. The other pad 60 is engaged inside the first one by means of a form fit so as to form a single unit.

Preferably the pads are made of a foamed material, such as foamed polypropylene, with a density of between 65 and 75 g/l or polystyrene, with a density of between 65 and 75 g/l.

The form fit is achieved by means of interlocking engagement of three projections 64, present on the surface of the pad 60, having preferably inverse tapered shape. The projections 64 are inserted inside corresponding cylindrical cavities 68 which are formed in the pad 62. The joining is further assisted by the use of an inverse taper on the cylindrical projections 64 with the widest part presented to the underside of the pad 60. The widest part of projections 64 is of a diameter slightly larger than the cylindrical cavities 68. When the pad 60, 62 are pushed together, the expanded foam material permits a small deformation allowing the wider part of the projection 64 to pass through the cavity 68 whereby it can then re-expands. This prevents the pad 60 from separating from the pad 62 unless a significant puffing force is applied to pad 60 by the user U.

It is possible and feasible to use pads of varying thickness, which the user selects depending on the shape of the shoulders when purchasing the collar, or to use more than one pad, associating a second pad and optionally a third pad with the first one. In this case, the first pad may have, in a position opposite to that of the projections 64, cylindrical cavities (and possible grooves) similar to those 68 which are provided in the pad 62. Owing to their removable and/or stackable property, the pads allow the collar 10 to be easily adapted to the body of the user U. It is sufficient to apply the pads with the most suitable size and/or shape in order to adapt the collar to one's personal needs. In particular, by means of the addition or replacement of one pad with another one it is possible to reduce the final distance between the upper surface of the segments 16, 18 and the helmet of the user U. Recent studies show that if, during an impact, the helmet does not readily make contact with the collar so as to transmit to it the axial pressure (i.e. the pressure which may cause permanent damage to the neck), the collar loses a lot of its effectiveness.

From the above description it is clear that the collar according to the present invention has characteristics such as to solve advantageously the problems and drawbacks of the devices according to the prior art.

It should also be noted that the top part of the collar is shaped with a particular curvature of the segments 16 and 18 such that the helmet worn by the user is able to rest readily laterally on the upper surface of the collar.

The present invention has been described with reference to a preferred embodiment, but conceptually and structurally equivalent solutions can be foreseen within the scope of the appended claims. For instance, the coupling of the lower pad 60 to the upper, fixed pad 62 can be obtained in different ways, such as by using additional or fewer cylindrical projections, or by the use of deliberate undercut features or dovetail joints to engage the two pieces together.

The invention claimed is:

1. Collar for protecting a neck of a user, useful for motorcycle riders, of the type comprising:
   two half-collars which are pivotably hinged together at one end so as to be rotatable in a substantial horizontal plane and which can be connected together by means of a fastening and release lever;
   a plate which at a rear of the collar extends downwards from a bottom edge of the collar such as to be centered with respect to a spinal column of the user;
   a protective shield which extends downwards at a front of the collar; and
   padding means intended to engage with shoulders of the user comprising a first pad wherein the padding means is intended to, engage with the user's shoulders while preventing any empty space from being introduced between the padding means and the user's shoulders permanently connected to bottom surfaces of said two half-collars in lateral zones thereof, said padding means comprising a second pad, the second pad being removable from said first pad and provided with means for fixing to said first pad, wherein said fixing means comprise projections formed on said second pad and able to cooperate with cavities formed in an opposite surface of said first pad.

2. The collar according to claim 1, wherein said padding means comprise a third pad, stacked with said first and second pad, wherein said second pad has, in a position opposite to that of its projections, cavities similar to those which are provided on said first pad and able to cooperate with the projections formed in an opposite surface of said third pad.

3. The collar of claim 1, wherein said pads can have different thicknesses.

4. The collar according to claim 1, wherein the first and second pads are shaped with a curvature corresponding to a profile of an underlying shoulder of the user.

5. The collar according to claim 1, wherein the first and second pads are made of foamed plastic.

6. The collar according to claim 5, wherein the projections have a diameter slightly larger than of the corresponding cavities, wherein the foamed plastic permits a small deformation which allows the projections to pass through the cavities.

7. The collar according to claim 1, wherein said projections have an inverted taper shape.

8. The collar according to claim 5, wherein said foamed plastic is selected among foamed polypropylene with a density of between 65 and 75 g/l and foamed polystyrene with a density of between 65 and 75 g/l.

9. The collar of claim 1, wherein the second pad is selectively removable and attachable from the first pad, wherein such removing and attaching operations require use of the first and second pads solely.

* * * * *

UNITED STATES PATENT AND TRADEMARK OFFICE
CERTIFICATE OF CORRECTION

Page 1 of 1

PATENT NO.           : 8,291,521 B2
APPLICATION NO.      : 12/743483
DATED                : October 23, 2012
INVENTOR(S)          : Giovanni Mazzarolo and Colin Ballantyne It is certified that error appears in the above-identified patent and that said Letters Patent is hereby corrected as shown below:

In the Claims

In claim 1, column 4, lines 2-5, the text "...wherein the padding means is intended to, engage with the user's shoulders while preventing any empty space from being introduced between the padding means and the user's shoulders..." should be deleted/removed, and at the end of claim 1, column 4, line 12, directly before the ".", the text ", wherein the padding means is intended to engage with the user's shoulders while preventing any empty space from being introduced between the padding means and the user's shoulders" should be added.

Signed and Sealed this
Fifth Day of August, 2014

Michelle K. Lee
*Deputy Director of the United States Patent and Trademark Office*